United States Patent [19]
Sokolsky et al.

[11] 3,974,085
[45] Aug. 10, 1976

[54] PROCESS FOR LIQUID PHASE PURIFICATION OF CARBIDE ACETYLENE AND COMPOSITIONS THEREFOR

[76] Inventors: Dmitry Vladimirovich Sokolsky, prospekt Abaya, 31, kv. 38; Yakov Avraamovich Dorfman, 7 mikroraion, 4, kv. 24; Irina Anatolievna Kazantseva, ulitsa Minusinskaya, 20b, kv. 12, all of Alma-Ata, U.S.S.R.

[22] Filed: Mar. 13, 1972

[21] Appl. No.: 234,394

[52] U.S. Cl. .................. 252/186; 48/216; 260/679 A; 423/224
[51] Int. Cl.² ............................................... C09K 3/00
[58] Field of Search .................. 252/186; 48/216; 280/679 A; 423/224

[56] References Cited
UNITED STATES PATENTS

| | | | |
|---|---|---|---|
| 850,010 | 4/1907 | Jaubert | 48/216 |
| 2,313,022 | 3/1943 | Rottmayr | 260/679 A |
| 2,407,332 | 9/1946 | Wearn et al. | 260/679 A |
| 2,673,885 | 3/1954 | Müller | 260/679 A |
| 2,908,546 | 10/1959 | Szatkowski | 48/216 X |

*Primary Examiner*—Harris A. Pitlick
*Attorney, Agent, or Firm*—Haseltine, Lake & Waters

[57] ABSTRACT

An oxidative aqueous solution for the purification of carbide acetylene that is acetylene, containing hydrogen phosphide and hydrogen sulphide admixtures, comprising cupric chloride, mercuric chloride and hydrochloric acid.

The proposed solution has a high activity and the ability of purifying a great amount of acetylene in one purification cycle before regeneration. One liter of the solution before regeneration purifies 300 – 6000 liters of carbide acetylene, that is, acetylene at a space velocity of 30 to 80 $min^{-1}$. The solution is noted for its stability.

In case of alternating the cycles of acetylene purification and solution regeneration 1 liter of this solution purifies 10000 to 30000 liters of acetylene without the additional introduction of the initial components into the solution.

1 Claim, No Drawings

PROCESS FOR LIQUID PHASE PURIFICATION OF CARBIDE ACETYLENE AND COMPOSITIONS THEREFOR

The present invention relates to a process of liquid phase purification of carbide acetylene, that is, acetylene, containing phosphide hydrogen phosphide hydrogen sulphide admixtures by oxidative aqueous solutions. Such admixtures are a poison for many catalysts employed in acetylene-based reactions.

An oxidative aqueous solution for purifying acetylene and comprising cupric chloride sodium chloride and potassium iodide is known. This solution can be repeatedly used after regeneration by blowing air through it for 1 – 2 hours.

A disadvantage of the known oxidative aqueous solution is its relatively low activity (space velocity of purification is 20 min$^{-1}$).

Another disadvantage is that the oxidative solution before regeneration (i.e., for one purification cycle) purifies only a relatively small quantity of gas (1 liter of the oxidative solution purifies only 560 liters of acetylene).

Moreover, a disadvantage of the known solution is that in case of alternating the acetylene purification and solution regeneration cycles, 1 liter of the solution purifies only 1560 liters of acetylene without an additional introduction of initial components into the solution.

An object of the present invention is the provision of an oxidative aqueous solution of higher activity for carbide acetylene, that is, acetylene, purification to remove hydrogen phosphide and hydrogen sulphide admixtures.

A further object of the invention is to provide an oxidative aqueous solution capable of purifying a greater amount of acetylene before regeneration (for one purification cycle).

A still further object of the invention is the provision of a more stable oxidative aqueous solution capable of purifying considerable quantities of carbide acetylene, that is, acetylene without an additional introduction of initial components into the solution.

In accordance with the stated objects and other objects which will be apparent from the following description thereof, the invention provides an oxidative aqueous solution comprising cupric chloride, mercuric chloride and hydrochloric acid for carbide acetylene purification from, that is, acetylene, purification to remove hydrogen phosphide and hydrogen sulphide admixtures.

It is recommended that the solution with the ingredients given above in following ratios (parts by weight) be used:

| | |
|---|---|
| cupric chloride | 100 – 200 |
| mercuric chloride | 10$^{-3}$ – 10$^{-2}$ |
| hydrochloric acid | 200 – 300 |
| water | 500 – 700 |

In order to reduce the consumption of hydrochloric acid a part of it can be replaced by cheaper sodium chloride. In this case, it is recommended that an oxidative aqueous solution with the ingredients in the following ratios (parts by weight) be used:

| | |
|---|---|
| cupric chloride | 100 – 200 |
| mercuric chloride | 10$^{-3}$ – 10$^{-2}$ |
| hydrochloric acid | 20 – 270 |
| sodium chloride | 180 – 30 |
| water | 500 – 700 |

An oxidative solution according to the invention has far better characteristics in comparison with the solution known heretofore. For example, one liter of the proposed solution before regeneration (i.e., for one purification cycle) purifies 3000 – 6000 liters of acetylene at a space velocity of 30 – 80 min$^{-1}$). In case of alternating the cycles of acetylene purification and solution regeneration 1 liter of the solution purifies 10000 – 30000 liters of acetylene without an additional introduction of the initial ingredients into the solution.

The oxidative solution of the invention comprises cupric chloride hydrochloric acid and mercuric chloride. In order to reduce the consumption of hydrochloric acid a part of it, as mentioned above, can be replaced by chloride. The ingredients enumerated above are dissolved in water at a temperature of 25° to 80°C in any sequence.

Spent solution is easily regenerated by blowing air for 1 – 2 hours. The degree of usage and regeneration of the solution can be adjusted and controlled potentiometrically by measuring the solution potential with a platinum electrode in relation to a calomel half-cell. Spent solution is characterized by a potential of 180 – 200 mV, while the regenerated solution potential is 380 to 420 mV. Thus, during acetylene purification the potential of the solution drops from 380 to 420 to 180 to 200 mV and during regeneration it increases from 180 to 200 mV to 380 to 420 mV.

For a better understanding of the present invention, the following illustrative examples are set forth. In the examples, all parts and percents are by weight unless otherwise indicated.

EXAMPLE 1

Into a reactor equipped with a nozzle there was fed an oxidative solution comprising 150 parts by weight of cupric chloride, 250 parts by weight of hydrochloric acid, 5.10$^{-3}$ parts by weight of mercuric chloride and 600 parts by weight of water. Through this solution at a temperature of 25°C, carbide acetylene, that is, acetylene containing 0.12 volume percent of hydrogen phosphide and 0.15 volume percent of hydrogen sulphide was passed at a space velocity of 50 min$^{-1}$. Before regeneration (for one purification cycle) 1 liter of the solution purified 4500 liters of acetylene. The spent solution was regenerated by blowing air through it for 1 – 2 hours. After regeneration the solution was again used for acetylene purification.

In case of alternating the cycles of purification and regeneration 1 liter of the said solution purified 30000 liters of acetylene without additional introduction of the initial components into the solution.

The degree of carbide acetylene, that is, acetylene, purification by removal of hydrogen phosphide and hydrogen sulphide admixtures equals 100%.

EXAMPLE 2

An oxidative aqueous solution comprising 150 parts by weight of cupric chloride 5.10$^{-3}$ parts by weight of mercuric chloride, 70 parts by weight of hydrochloric acid, 180 parts by weight of sodium chloride and 600 parts by weight of water was tested under the same conditions as those given in Example 1.

The performance characteristics of the solution were the same as in Example 1.

EXAMPLE 3

An oxidative aqueous solution comprising 100 parts by weight of cupric chloride, 200 parts by weight of hydrochloric acid, $10^{-2}$ parts by weight of mercuric chloride and 700 parts by weight of water was tested under the same conditions as in Example 1. In case of using such a solution the space velocity of acetylene purification was 40 $\min^{-1}$.

Before regeneration (for one purification cycle) 1 liter of the solution purified 3500 liters of acetylene. In case of alternating the cycles of purification and regeneration 1 liter of the solution having the composition given above purified 18000 liters of acetylene without additional introduction of the initial components into the solution.

The degree of carbide acetylene, that is, acetylene, purification by removal of hydrogen phosphide and hydrogen sulphide admixture equals 100%.

EXAMPLE 4

An oxidative aqueous solution comprising 200 parts by weight of cupric chloride, 300 parts by weight of hydrochloric acid, $10^{-3}$ parts by weight of mercuric chloride and 500 parts by weight of water was tested under the same conditions as those given in Example 1. In use such a solution exhibited a space velocity of acetylene purification was 60 $\min^{-1}$. Before regeneration (for one cycle of purification) 1 liter of the solution purified 6000 liters of acetylene. In case of alternating the cycles of purification and regeneration 1 liter of the solution purified 25000 liters of acetylene without additional introduction of the initial components into the solution.

The degree of carbide acetylene, that is, acetylene, purification by removal of hydrogen phosphide and hydrogen sulphide admixtures equals 100%.

EXAMPLE 5

An oxidative aqueous solution comprising 150 parts by weight of cupric chloride, $5.10^{-3}$ parts by weight of mercuric chloride, 20 parts by weight of hydrochloric acid, 180 parts by weight of sodium chloride and 600 parts by weight of water was tested under the same conditions as in Example 1. In use the solution exhibited a space velocity of acetylene purification of 40 $\min^{-1}$. Before regeneration (for one purification cycle) 1 liter of the solution purified 4500 liters of acetylene. In case of alternating the cycles of purification and regeneration 1 liter of the solution purified 18000 liters of acetylene without an additional introduction of the initial components into the solution.

The degree of carbide acetylene, that is, acetylene, purification by removal of hydrogen phosphide and hydrogen sulphide equals 100%.

EXAMPLE 6

An oxidative aqueous solution comprising 200 parts by weight of cupric chloride, $10^{-3}$ parts by weight of mercuric chloride, 270 parts by weight of hydrochloric acid, 30 parts by weight of sodium chloride and 600 parts by weight of water was tested under the same conditions as in Example 1. In use the solution exhibited a space velocity of acetylene purification of 60 $\min^{-1}$. Before regeneration (for one purification cycle), 1 liter of the solution purified 6000 liter of acetylene. In case of alternating the cycles of purification and regeneration, 1 liter of the an solution purified 25000 liters of acetylene without an additional introduction of the initial components into the solution.

The degree of carbide acetylene, that is, acetylene purification by removal of hydrogen phosphide and hydrogen sulphide admixtures equals 100%.

We claim:

1. A highly active oxidative aqueous solution for acetylene purification which removes hydrogen phosphide and hydrogen sulfide admixture from said acetylene, said solution consisting of 100 to 200 parts by weight of cupric chloride, $10^{-3}$ to $10^{-2}$ part by weight of mercuric chloride and 200 to 300 parts by weight of hydrochloric acid, said hydrochloric acid being replaceable by sodium chloride, in amounts from 180–30 parts by weight and water in from 500 to 700 parts by weight.

* * * * *